(12) United States Patent
May et al.

(10) Patent No.: US 10,492,834 B2
(45) Date of Patent: Dec. 3, 2019

(54) SURGICAL INSTRUMENT SYSTEM AND METHOD

(71) Applicant: Warsaw Orthopedic, Inc., Warsaw, IN (US)

(72) Inventors: Jason M. May, Cordova, TN (US); William A. Rezach, Atoka, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 731 days.

(21) Appl. No.: 14/645,148

(22) Filed: Mar. 11, 2015

(65) Prior Publication Data
US 2016/0262819 A1   Sep. 15, 2016

(51) Int. Cl.
*A61B 17/88* (2006.01)
*A61B 17/70* (2006.01)
*A61B 17/86* (2006.01)

(52) U.S. Cl.
CPC ........ *A61B 17/7035* (2013.01); *A61B 17/861* (2013.01); *A61B 17/8615* (2013.01); *A61B 17/8888* (2013.01)

(58) Field of Classification Search
CPC ...................................... A61B 17/88
See application file for complete search history.

(56) References Cited

U.S. PATENT DOCUMENTS

| | | | |
|---|---|---|---|
| 7,691,132 B2 * | 4/2010 | Landry | A61B 17/1604 606/279 |
| 2010/0312279 A1 * | 12/2010 | Gephart | A61B 17/3421 606/264 |
| 2013/0053895 A1 * | 2/2013 | Stoll | A61B 17/8028 606/279 |

* cited by examiner

*Primary Examiner* — Matthew W Schall

(57) ABSTRACT

A surgical implant driver includes a member that defines a longitudinal axis and includes a first mating surface and a second mating surface spaced from the first mating surface.

19 Claims, 5 Drawing Sheets

SURGICAL INSTRUMENT SYSTEM AND METHOD

TECHNICAL FIELD

The present disclosure generally relates to medical devices for the treatment of musculoskeletal disorders, and more particularly to a surgical system and method for treating a spine.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs, which include implants such as bone fasteners, connectors, plates and vertebral rods are often used to provide stability to a treated region. These implants can redirect stresses away from a damaged or defective region while healing takes place to restore proper alignment and generally support the vertebral members. Surgical instruments are employed, for example, to engage the fasteners for attachment to the exterior of two or more vertebral members. This disclosure describes an improvement over these prior art technologies.

SUMMARY

In one embodiment, a surgical instrument is provided. The surgical instrument includes a member that defines a longitudinal axis and includes a first mating surface and a second mating surface spaced from the first mating surface. In some embodiments, systems and methods are disclosed.

BRIEF DESCRIPTION OF THE DRAWINGS

The present disclosure will become more readily apparent from the specific description accompanied by the following drawings, in which.

DETAILED DESCRIPTION

Figure 1:
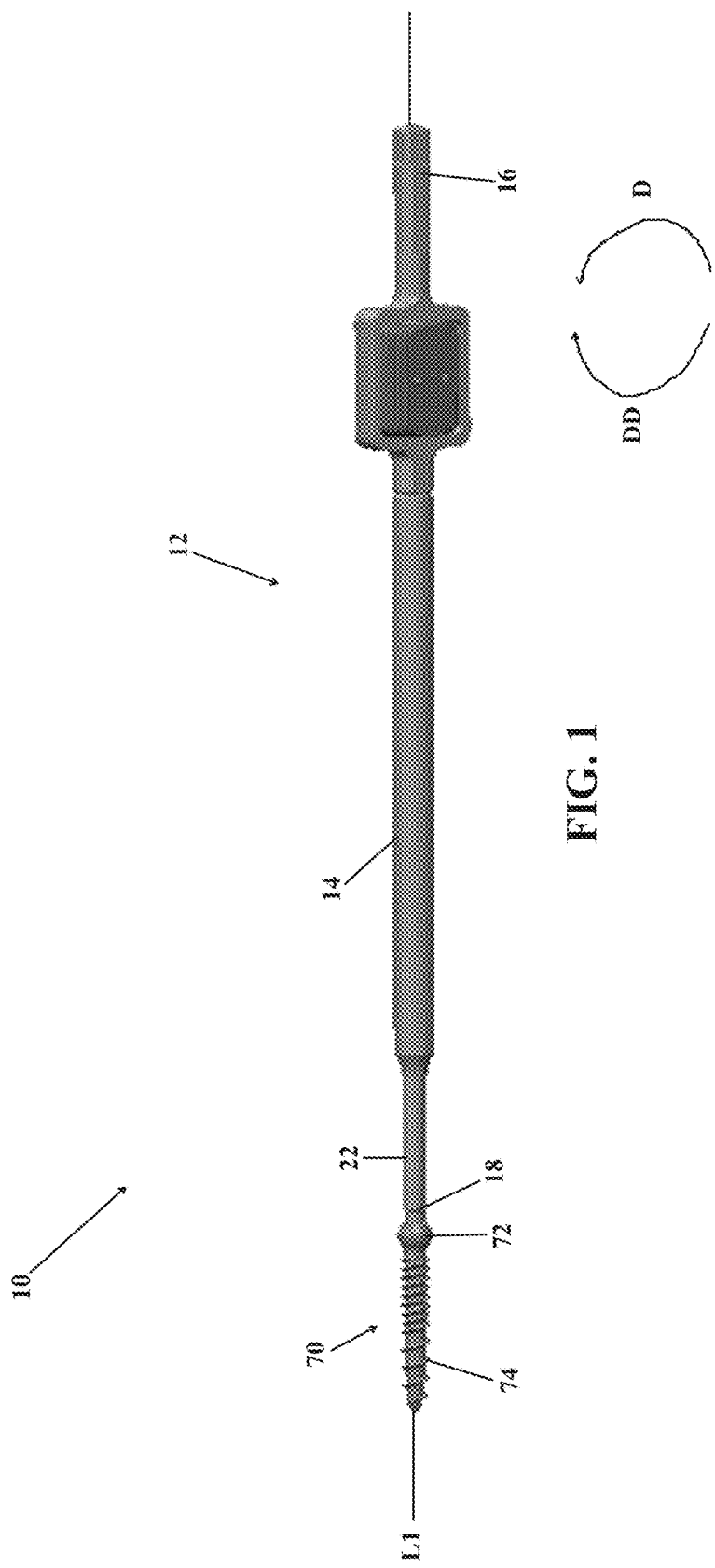
FIG. 1 is a perspective view of components of one embodiment of a surgical system in accordance with the principles of the present disclosure.

The exemplary embodiments of a surgical system are discussed in terms of medical devices for the treatment of musculoskeletal disorders and more particularly, in terms of a surgical system and a method for treating a spine. In some embodiments, the system comprises a surgical instrument and related methods of use, which can be employed with spinal constructs including bone fasteners and connectors. In some embodiments, the surgical instrument can be employed with multiple types of receivers and/or screw heads.

In one embodiment, the system includes a surgical instrument, such as, for example, a bone screw driver configured to interact with a shank of a bone screw and/or a receiver or head of a bone screw. In one embodiment, the system includes a driver configured to thread into a bone screw component and provide a rigid interface between the driver and the bone screw component.

In one embodiment, the system includes a driver configured for use with or without a tulip head or receiver on a bone screw. In one embodiment, the system includes a driver including a mating surface, such as, for example, a spline interface configured to facilitate a rigid and/or strong interface with a bone screw. In one embodiment, the spline interface is disposed with a forward facing surface of the driver. In one embodiment, the spline interface is radially disposed about a distal end of the driver. In one embodiment, the mating surface of the driver engages a mating surface of the bone screw to resist, minimize and/or prevent toggle between the components.

In one embodiment, the system includes a driver that can be employed with a bone screw having a cannulated shaft and/or a bone screw having a solid shaft. In one embodiment, the system includes a driver having a drive and/or mating surface that can be employed with and/or configured for mating engagement with a bone screw having a hexagonal and/or a torx shaped socket to allow the driver to engage the bone screw to adjust its height with a penetrated surface, such as, for example, bone. In one embodiment, the system includes a driver configured for a threaded engagement with an opening of a bone screw.

In one embodiment, the system includes a driver having a square and/or rectangular drive. In one embodiment, the driver is configured for engagement with a bone screw with or without a receiver defining an implant cavity, which may be configured for disposal of a spinal rod. In one embodiment, the driver is configured for threaded engagement with the bone screw to minimize toggle. In one embodiment, the system includes a driver configured for engagement with a bone screw having a square or rectangle socket to increase strength. In one embodiment, the system includes a driver having a T25 drive to engage a socket in a bone screw.

In one embodiment, the system includes a driver configured to engage a 12 point socket that allows interaction with a standard T25 drive and accepts a 12 point drive configured to deliver additional torque. In one embodiment, the system includes a driver configured with a threaded interface for engagement with a bone screw.

In one embodiment, the system includes a driver configured to deliver a higher capacity of torque while preventing sheering. In one embodiment, the system includes a driver configured to increase torque and facilitate utilization of a bone screw without a receiver connected to a head portion of the screw.

In one embodiment, the system includes a driver configured with radial splines configured to engage radial splines on a head of a bone screw. In one embodiment, the splines center and align the driver as well as provide a robust connection of the components parts. In one embodiment, the system includes a driver having an internal threaded shaft configured to facilitate engagement of the splined surfaces. In one embodiment, the system includes a driver having a tapered splined surface. In one embodiment, the system includes a driver having a rectangular shaped engagement to provide an increased torque.

In some embodiments, the system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the system of the present disclosure may be employed with other osteal and bone related applications, including those associated with diagnostics and therapeutics. In some embodiments, the disclosed system may be alternatively employed in a surgical treatment with a patient in a prone or supine position, and/or employ various surgical approaches to the spine, including anterior, posterior, posterior mid-line, direct lateral, postero-lateral, and/or anterolateral approaches, and in other body regions. The system of the present disclosure may also be alternatively employed with procedures for treating the lumbar, cervical, thoracic, sacral and pelvic regions of a spinal column. The system of the present disclosure may also be used on animals, bone models and other non-living substrates, such as, for example, in training, testing and demonstration.

The system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system including a surgical instrument, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-4, there are illustrated components of a surgical system 10, in accordance with the principles of the present disclosure.

The components of system 10 can be fabricated from biologically acceptable materials suitable for medical applications, including metals, synthetic polymers, ceramics and bone material and/or their composites. For example, the components of system 10, individually or collectively, can be fabricated from materials such as stainless steel alloys, aluminum, commercially pure titanium, titanium alloys, Grade 5 titanium, superelastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TOP), hydroxyapatite (HA)-TCP, calcium sulfate, or other resorbable polymers such as polyaetide, polyglycolide, polytyrosine carbonate, polycaroplaetohe and their combinations. Various components of system 10 may have material composites, including the above materials, to achieve various desired characteristics such as strength, rigidity, elasticity, compliance, biomechanical performance, durability and radiolucency or imaging preference. The components of system 10, individually or collectively, may also be fabricated from a heterogeneous material such as a combination of two or more of the above-described materials. The components of system 10 may be monolithically formed, integrally connected or include fastening elements and/or instruments, as described herein.

System 10, which includes a surgical instrument, such as, for example, a driver 12, is employed, for example, with an open or mini-open, minimal access and/or minimally invasive including percutaneous surgical technique to deliver and fasten an implant at a surgical site within a body of a patient, for example, a section of a spine. In one embodiment, the components of system 10 are configured to fix a bone fastener with tissue for a surgical treatment to treat various spine pathologies, such as those described herein.

Driver 12 includes a shaft 14 extending along a longitudinal axis L1 between an end 16 and an end 18. In some embodiments, shaft 14 may be variously configured and dimensioned, such as, for example, planar, concave, convex or polygonal. End 16 is configured to engage an actuator, such as, for example, a surgical instrument, powered drill, hand drill, driver or other tool to rotate driver 12, in the direction shown by arrow D and/or the direction shown by arrow DD. In one embodiment, end 16 has a square cross sectional configuration and is configured to engage a correspondingly shaped portion of the actuator. In some embodiments, end 16 may include an oval, oblong, triangular, square or polygonal cross sectional configuration configured engage a correspondingly shaped portion of the actuator. In one embodiment, end 16 includes an interchangeable driving handle removably connected to end 16 such that torque applied manually or by motorized means to the handle is transmitted to end 16.

Figure 2:
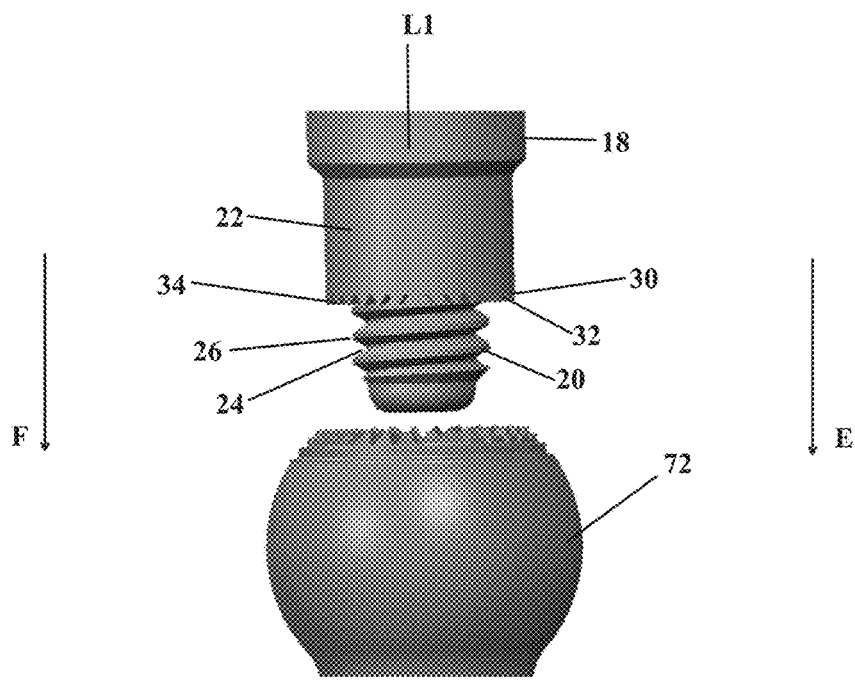
FIG. 2 is a break away view of components shown in FIG. 1.
Figure 3:
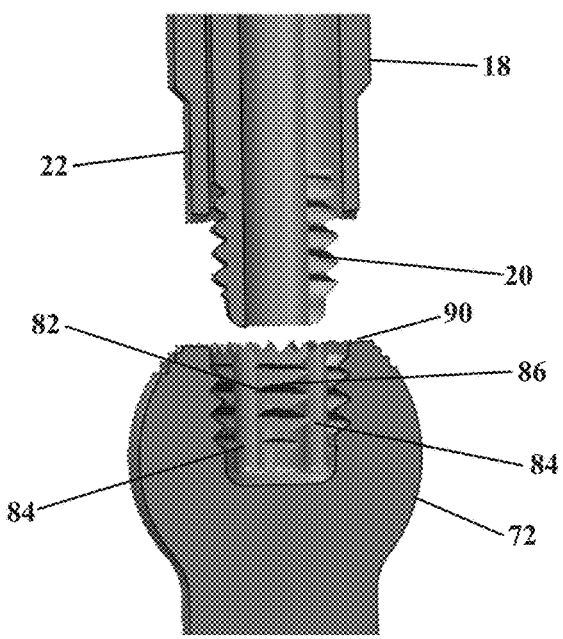
FIG. 3 is a cross section view of the components shown in FIG. 2.

End 18 includes a mating surface, such as, for example, a projection 20 and a mating surface, such as, for example, a sleeve 22. As shown in FIG. 2, projection 20 extends from end 18 along axis L1. In some embodiments, projection 20 may extend in various orientations, such as, for example, transverse, series, parallel, offset or staggered. Projection 20 includes an outer surface 24. Surface 24 includes a threaded engagement surface 26 configured for engagement with a receiving portion of an implant, such as, for example, a bone fastener 70. Surface 26 is configured to engage fastener 70 such that toggling is reduced. In some embodiments, projection 20 may be variously configured and dimensioned, such as, for example, irregular, uniform, non-uniform, staggered, tapered, consistent or variable.

Sleeve 22 extends along a portion of shaft 14. Sleeve is circumferentially disposed about shaft 14. In some embodiments, sleeve 22 may be variously configured and dimensioned, such as, for example, irregular, uniform, non-uniform, staggered, tapered, consistent or variable. Sleeve 22 includes an end 30 having an end facing surface 32 oriented transverse to axis L1. Surface 32 includes a spline surface 34 disposed radially about surface 32 and configured for engagement with a receiving portion of fastener 70. Surface 34 is configured to engage fastener 70 such that a fixed and/or locked interface between driver 12 and fastener 70 is achieved. In one embodiment, sleeve 22 is configured for translation relative to shaft 14. In one embodiment, sleeve 22 is fixed with shaft 14 such that projection 20 extends a distance from surface 32 to facilitate engagement of projection 20 with fastener 70.

Fastener 70 includes a head 72 configured for attachment with driver 12 and an elongated shaft 74 configured for penetrating tissue. Shaft 74 has a cylindrical cross section configuration and includes an outer surface having an external thread form. In some embodiments, the thread form may include a single thread turn or a plurality of discrete threads. In some embodiments, other engaging structures may be disposed on shaft 74, such as, for example, a nail configuration, barbs, expanding elements, raised elements and/or spikes to facilitate engagement of shaft 74 with tissue, such as, for example, vertebrae.

In some embodiments, all or only a portion of shaft 74 may have alternate cross section configurations, such as, for example, oval, oblong, triangular, square, polygonal, irregular, uniform, non-uniform, offset, staggered, undulating, arcuate, variable and/or tapered. In some embodiments, the outer surface may include one or a plurality of openings. In some embodiments, all or only a portion of the outer surface may have alternate surface configurations to enhance fixation with tissue such as, for example, rough, arcuate, undulating, mesh, porous, semi-porous, dimpled and/or textured. In some embodiments, all or only a portion of shaft 74 may be disposed at alternate orientations, relative to a longitudinal axis of fastener 70, such as, for example, transverse, perpendicular and/or other angular orientations such as acute or obtuse, co-axial and/or may be offset or staggered. In some embodiments, all or only a portion of shaft 74 may be cannulated.

Head 72 comprises a spherical configuration. Head 72 includes an outer circumferential surface 76 having a substantially uniform diameter thereabout. In some embodiments, all or only a portion of surface 76 includes a spherical configuration. Head 72 includes an inner surface 80 that defines a mating surface receiving portion, such as, for example a socket 82. Socket 82 is configured for disposal of an instrument and/or tool extension, such as, for example, end 18 of driver shaft 14, as discussed herein. Socket 82 includes a circumference and a plurality of lobes 84 disposed thereabout. Lobes 84 are uniformly spaced apart about the circumference of surface 80. Adjacent lobes 84 are connected by arcuate portions 86. In one embodiment, portion 86 include a threaded surface configured for engagement with threaded surface 26 of projection 20 for fixation of driver 12 with fastener 70. Socket 82 has a hollow cross section configured for disposal of projection 20 such that rotation of driver 12, in the direction shown by arrow D or the direction shown by arrow DD, causes rotation of fastener 70, in the direction shown by arrow D or the direction shown by arrow DD.

In one embodiment, socket 82 includes a hexagonal cross sectional configuration and is configured to engage a correspondingly shaped driver. In some embodiments, socket 82 may include an oval, oblong, triangular, square or polygonal cross sectional configuration configured engage a correspondingly shaped portion of a standard driver.

Figure 4:
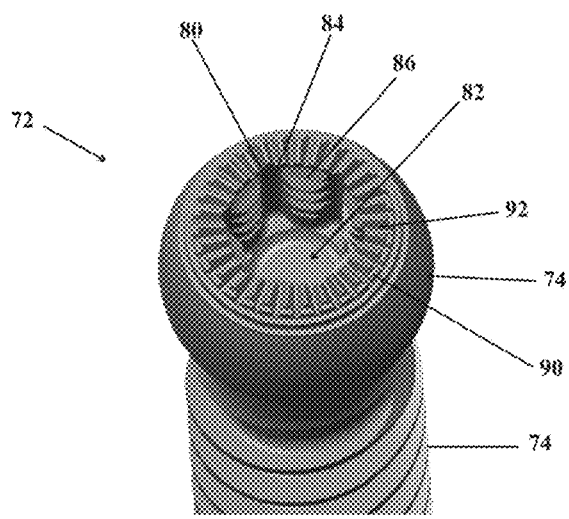
FIG. 4 is a break away perspective view of components shown in FIG.
Figure 5:
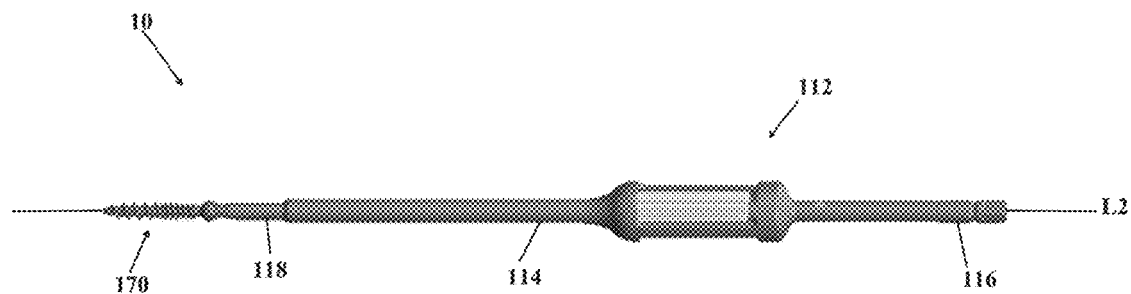
FIG. 5 is a perspective view of components of one embodiment of a surgical system in accordance with the principles of the present disclosure.
Figure 6:
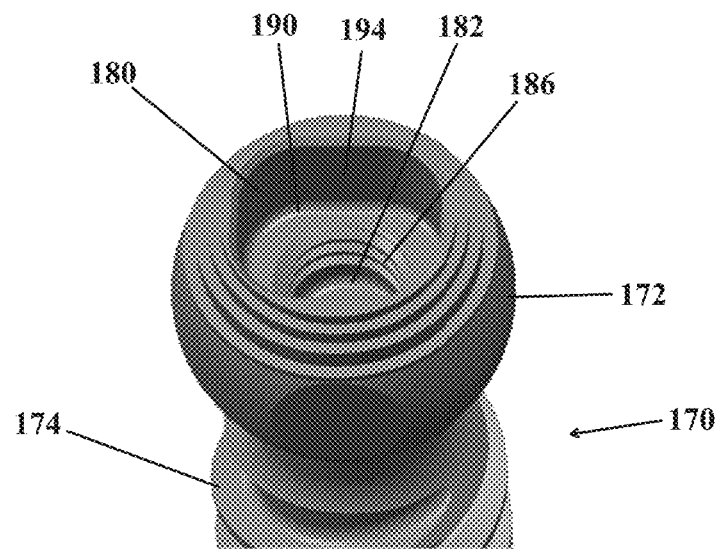
FIG. 6 is a break away perspective view of a component of one embodiment of a surgical system in accordance with the principles of the present disclosure.

Head 72 includes a mating surface receiving portion, such as, for example, a proximal face 90 extending perpendicular to axis L1. Face 90 defines socket 82. In some embodiments, face 90 and/or socket 82 may be disposed at alternate orientations relative to axis L1, such as, for example, transverse, perpendicular and/or other angular orientations such as acute or obtuse. In some embodiments, face 90 may be variously configured and dimensioned, such as, for example, concave, convex, irregular, uniform, non-uniform, staggered, tapered, consistent or variable. Face 90 includes a spline surface 92 disposed radially about face 90 and configured for engagement with surface 34 of sleeve 22. As shown in FIG. 4, surface 92 extends circumferentially around socket 82. Surface 34 engages surface 92 to form a rigid connection between driver 12 and fastener 72 to increase a torque applied to fastener 70.

In assembly, operation and use, system 10, similar to the systems and methods described herein, is employed with a surgical procedure for treatment of a spinal disorder affecting a section of a spine of a patient, as discussed herein. For example, system 10 can be used with a surgical procedure for treatment of a condition or injury of an affected section of the spine including vertebrae (not shown). In some embodiments, one or all of the components of system 10 can be delivered or implanted as a pre-assembled device or can be assembled in situ. System 10 may be completely or partially revised, removed or replaced.

For example, system 10 can be employed with a surgical treatment of an applicable condition or injury of an affected section of a spinal column and adjacent areas within a body, such as, for example, vertebrae. It is envisioned that system 10 may be employed with one or a plurality of vertebra. To treat a selected section of the vertebrae, a medical practitioner obtains access to a surgical site including the vertebrae in any appropriate manner, such as through incision and retraction of tissues. In some embodiments, system 10 can be used in any existing surgical method or technique including open surgery, mini-open surgery, minimally invasive surgery and percutaneous surgical implantation, whereby the vertebrae are accessed through a mini-incision, or sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for implantation of components of system 10. A preparation instrument (not shown) can be employed to prepare tissue surfaces of the vertebrae, as well as for aspiration and irrigation of a surgical region.

A pilot hole or the like is made in a selected vertebra of the vertebrae for receiving a fastener 70. System 10 is disposed adjacent the vertebrae at a surgical site and the components of system 10 including driver 12, are manipulable to drive, torque, insert or otherwise connect fastener 70 to the vertebra. Driver 12 is translated axially relative to fastener 70, in the direction shown by arrow E in FIG. 2, such that surface 26 of projection 20 mates with surface 84 of socket 82 to matingly and releasably fix driver 12 with fastener 70. Sleeve 22 is translated along shaft 14, in the direction shown by arrow F in FIG. 2, and manipulated to engage surface 34 with surface 92 to matingly and releasably fix driver 12 with fastener 70. Fastener 70 is inserted into the vertebra with driver 12, for example, by rotating driver 12, in the direction shown by arrow D or the direction shown by arrow DD in FIG. 1, which causes rotation of fastener 70, in the direction shown by arrow D or the direction shown by arrow DD. As fastener 70 rotates, in the direction shown by arrow D and the direction shown by arrow DD, fastener 70 translates within the vertebra. Upon completion of a surgical procedure, driver 12 may be disengaged from fastener 70.

Surgical instrument 12 may be re-assembled for use in a surgical procedure. In some embodiments, surgical instrument 12 may comprise various instruments including the mating configurations described herein, with, for example, inserters, extenders, reducers, spreaders, distractors, blades, retractors, clamps, forceps, elevators and drills, which may be alternately sized and dimensioned, and arranged as a kit.

Upon completion of a procedure, surgical instrument 12, surgical instruments and/or tools, assemblies and non-implanted components of system 10 are removed and the incision(s) are closed. One or more of the components of system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of system 10. In some embodiments, system 10 may include one or a plurality of plates, connectors and/or bone fasteners for use with a single vertebral level or a plurality of vertebral levels.

In one embodiment, as shown in FIGS. 5-8, surgical system 10, similar to the systems and methods described herein, comprises a surgical instrument, such as, for example, a driver 112, similar to driver 12 described herein, and fastener 170, similar to fastener 70 described herein. Driver 112 includes a shaft 114 extending along a longitudinal axis L2 between an end 116 and an end 118. End 116 is configured to engage an actuator, described herein.

Figure 7:
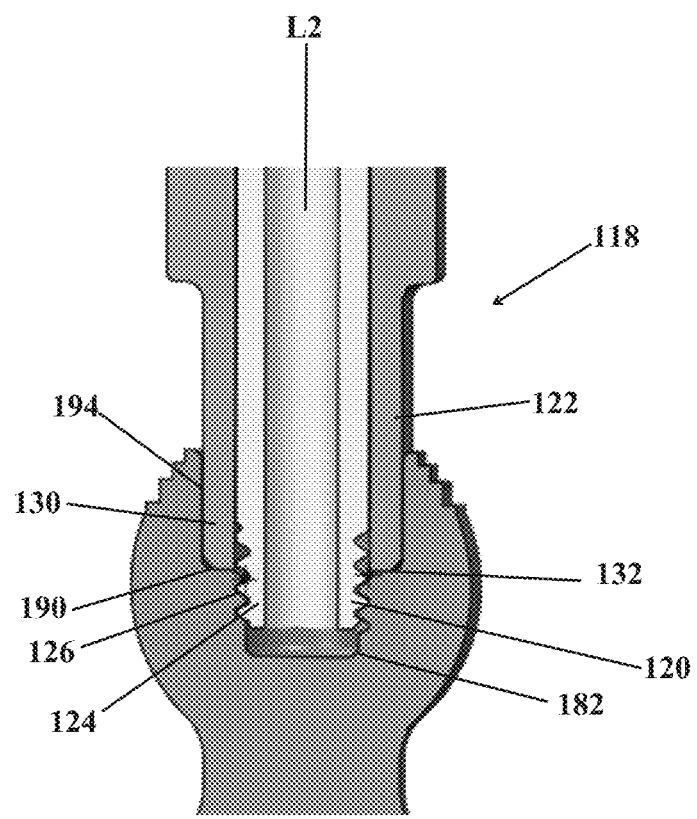
FIG. 7 is a break away cross section view of components of one embodiment of a surgical system in accordance with the principles of the present disclosure.

End 118 includes a projection 120 and a sleeve 122. As shown in FIG. 7, projection 120 extends from end 118 along axis L2. Projection 120 includes an outer surface 124. Surface 124 includes a threaded engagement surface 126 configured for engagement with a receiving portion of an implant, such as, for example, bone fastener 170.

Sleeve 122 extends along a portion of shaft 114. Sleeve 122 includes an end 130 having a surface 134. Surface 134 is configured to engage an engagement surface of fastener 170, as described herein. In one embodiment, sleeve 122 includes a rectangular cross sectional configuration. In some embodiments, sleeve 122 may include an oval, oblong, triangular, square or polygonal cross sectional configuration.

Fastener 170 includes a head 172 configured for attachment with driver 112 and an elongated shaft 174 configured for penetrating tissue. Head 172 comprises a spherical configuration. Head 172 includes an inner surface 180 that defines a mating surface receiving portion, such as, for example a socket 182. Socket 182 includes a threaded surface 186 configure for engagement with threaded surface 126 of projection 120. Socket 182 has a hollow cross section configured for disposal of projection 120 such that rotation of driver 112 causes rotation of fastener 170.

Figure 8:
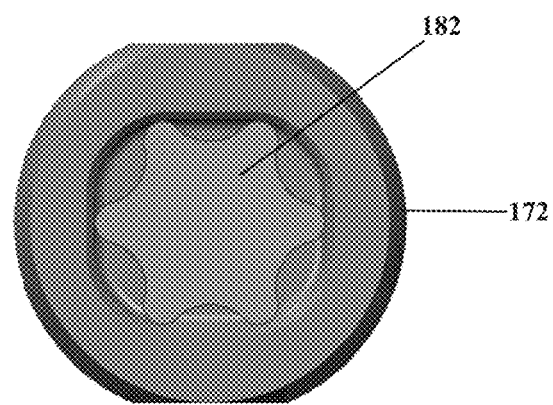
FIG. 8 is an end view of a component of one embodiment of a surgical system in accordance with the principles of the present disclosure.

In one embodiment, as shown in FIG. 8, socket 182 includes a hexalobe cross sectional configuration and is configured to engage a correspondingly shaped driver. In some embodiments, socket 182 may include an oval, oblong, triangular, square or polygonal cross sectional configuration configured engage a correspondingly shaped portion of a standard driver.

Head 172 includes an engagement surface, such as, for example, a proximal face 190, which defines socket 182. Face 190 forms a cavity 194 configured to receive sleeve 122. Cavity 194 includes a rectangular cross sectional configuration corresponding to sleeve 122. In some embodiments, cavity 194 may include an oval, oblong, triangular, square or polygonal cross sectional configuration. In some embodiments, an outer surface of head 172 comprises a mating surface, such as, for example, threads configured for fixed and/or locking engagement with a distal end of driver 112 to define a rigid connection between driver 112 and fastener 170.

Figure 9:
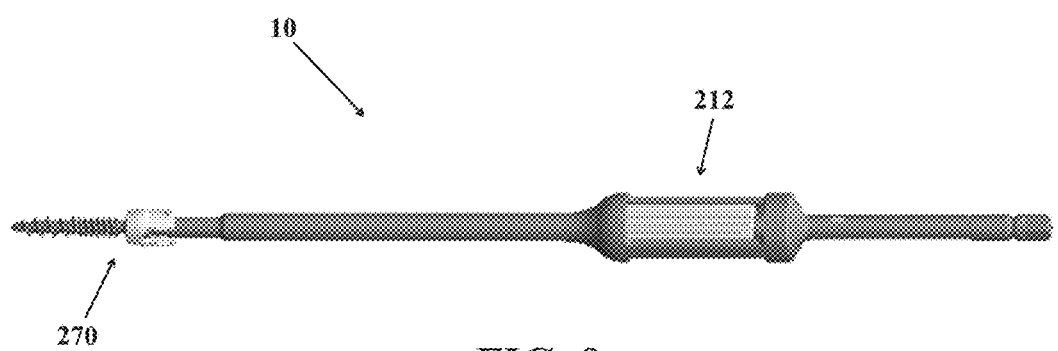
FIG. 9 is a perspective view of components of one embodiment of a surgical system in accordance with the principles of the present disclosure.

In one embodiment, as shown in FIG. 9, surgical system 10, similar to the systems and methods described herein, comprises a surgical instrument, such as, for example, a driver 212, similar to driver 12 described herein, and a fastener 270, similar to fastener 70 described herein. Fastener 270 includes a receiver defining an implant cavity, such as, for example, a tulip shaped head. In some embodiments, fasteners 270 can include various bone fasteners, mono-axial screws, sagittal angulation screws, fixed screws, uni-planar screws, pedicle screws or multi-axial screws used in spinal surgery.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
   a member including a sleeve defining a longitudinal axis, the sleeve including a first mating surface, the member comprising a shaft movably disposed in the sleeve, the shaft including a second mating surface spaced from the first mating surface, the first mating surface comprising a spline interface; and
   a handle removably connected to the member such that torque applied manually or by motorized means to the handle is transmitted to the member.

2. A surgical instrument as recited in claim 1, wherein the second mating surface includes a threaded engagement surface.

3. A surgical instrument as recited in claim 1, wherein the surgical instrument is a driver configured for engagement with a fastener.

4. A surgical instrument as recited in claim 1, wherein the second mating surface is configured for engagement with a mating surface receiving portion disposed in a head of a fastener.

5. A surgical instrument as recited in claim 1, wherein the first mating surface is configured for engagement with a mating surface receiving portion disposed around a head of a fastener.

6. A surgical instrument as recited in claim 1, wherein the second mating surface translates relative to the first mating surface.

7. A surgical instrument as recited in claim 1, wherein the spline interface includes a rectangular shaped surface.

8. A surgical instrument as recited in claim 1, wherein the second mating surface extends beyond the first mating surface.

9. A surgical instrument as recited in claim 1, wherein the sleeve extends along the longitudinal axis between a first end surface and an opposite second end surface, the second end surface including the first mating surface.

10. A surgical instrument as recited in claim 9, wherein the second end surface extends perpendicular to the longitudinal axis.

11. A surgical instrument as recited in claim 1, wherein the sleeve extends along the longitudinal axis between a proximal and an opposite distal end, the spline interface being radially disposed about the distal end.

12. A surgical instrument as recited in claim 11, wherein the second mating surface includes a threaded engagement surface, the second mating surface extending beyond the first mating surface.

13. A surgical instrument as recited in claim 11, wherein the proximal end has a square cross sectional configuration and is configured to engage a correspondingly shaped portion of an actuator.

14. A surgical instrument as recited in claim 11, wherein the handle is removably connected to the proximal end.

15. A surgical instrument as recited in claim 1, wherein the shaft is cannulated.

16. A surgical instrument as recited in claim 1, wherein the shaft has a blunt tip that includes the second mating surface, the second mating surface defining a threaded outer surface of the shaft.

17. A surgical instrument as recited in claim 1, wherein the shaft is configured to translate within the sleeve along the longitudinal axis.

18. A surgical instrument comprising:
    a member including a sleeve extending along a longitudinal axis between a proximal end and an opposite distal end, the distal end including an end surface that extends perpendicular to the longitudinal axis, the end surface including a spline interface radially disposed about the distal end, the member including a cannulated shaft movably disposed in the sleeve, the shaft including a threaded outer surface that extends beyond the end surface; and
    a handle removably connected to the member such that torque applied manually or by motorized means to the handle is transmitted to the member.

19. A surgical instrument comprising:
    a member including a sleeve extending along a longitudinal axis between a proximal end and an opposite distal end, the distal end having a spline interface and a rectangular cross sectional configuration, the member including a cannulated shaft movably disposed in the sleeve, the shaft including a threaded outer surface that extends beyond the distal end; and
    a handle removably connected to the member such that torque applied manually or by motorized means to the handle is transmitted to the member.

* * * * *